United States Patent
Jacob et al.

(10) Patent No.: US 9,526,468 B2
(45) Date of Patent: Dec. 27, 2016

(54) MULTIPLE FRAME ACQUISITION FOR EXPOSURE CONTROL IN X-RAY MEDICAL IMAGERS

(71) Applicant: General Electric Company, Schenectady, NY (US)

(72) Inventors: Biju Jacob, Niskayuna, NY (US); Remy Andre Klausz, Yvelines (FR); John Eric Tkaczyk, Niskayuna, NY (US); Emad Abutabanjeh, Waukesha, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 94 days.

(21) Appl. No.: 14/481,494

(22) Filed: Sep. 9, 2014

(65) Prior Publication Data

US 2016/0066875 A1 Mar. 10, 2016

(51) Int. Cl.
*A61B 6/00* (2006.01)
*G06T 7/20* (2006.01)

(52) U.S. Cl.
CPC ............ *A61B 6/5264* (2013.01); *A61B 6/4208* (2013.01); *A61B 6/4405* (2013.01); *A61B 6/467* (2013.01); *A61B 6/486* (2013.01); *A61B 6/487* (2013.01); *A61B 6/502* (2013.01); *A61B 6/5229* (2013.01); *A61B 6/542* (2013.01); *G06T 7/2053* (2013.01); *A61B 6/4233* (2013.01); *G06T 2207/10116* (2013.01)

(58) Field of Classification Search
CPC ..... A61B 6/4208; A61B 6/4233; A61B 6/486; A61B 6/487; A61B 6/502; A61B 6/5205; A61B 6/54; A61B 6/542; A61B 6/5264

USPC ................. 378/37, 42, 98.7, 98.12
See application file for complete search history.

(56) References Cited

U.S. PATENT DOCUMENTS

| 4,647,956 A | 3/1987 | Shrivastava et al. |
| 5,081,664 A | 1/1992 | Lie et al. |
| 5,125,018 A * | 6/1992 | Asahina ............. A61B 6/481 348/E5.089 |
| 5,224,141 A * | 6/1993 | Yassa ................. H04N 5/32 348/E5.086 |

(Continued)

FOREIGN PATENT DOCUMENTS

| DE | 4025427 A1 | 2/1992 |
| DE | 4420603 C1 | 6/1995 |

(Continued)

OTHER PUBLICATIONS

Bonnet et al., "Dynamic X-Ray Computed Tomography", Proceedings of IEEE, Volume No. 91, Issue No. 10, pp. 1574-1587, Oct. 2003.

(Continued)

*Primary Examiner* — Allen C. Ho
(74) *Attorney, Agent, or Firm* — Buckley, Maschoff & Talwalkar, LLC

(57) ABSTRACT

According to some embodiments, a method and a system to create a medical image are disclosed. The method comprises receiving a plurality of patient tissue images during an x-ray dose. Furthermore, during the x-ray dose, a determination is made if motion occurred in the plurality of patient tissue images. In a case that no motion is determined, a diagnostic image of the patient tissue comprising the plurality of patient tissue images is created.

13 Claims, 5 Drawing Sheets

(56) References Cited

U.S. PATENT DOCUMENTS

| | | | |
|---|---|---|---|
| 5,400,383 A * | 3/1995 | Yassa | H04N 5/32 348/E5.086 |
| 5,467,380 A | 11/1995 | De Jonge et al. | |
| 5,528,043 A * | 6/1996 | Spivey | A61B 6/4233 250/208.1 |
| 5,530,266 A * | 6/1996 | Yonehara | G02F 1/13454 257/347 |
| 5,625,210 A | 4/1997 | Lee et al. | |
| 5,777,335 A | 7/1998 | Mochizuki et al. | |
| 5,801,385 A | 9/1998 | Endo et al. | |
| 5,859,892 A * | 1/1999 | Dillen | H04N 5/235 348/E5.034 |
| 5,881,184 A | 3/1999 | Guidash | |
| 5,903,021 A | 5/1999 | Lee et al. | |
| 5,917,883 A * | 6/1999 | Khutoryansky | A61B 6/08 378/116 |
| 5,929,499 A | 7/1999 | Kuhlmann et al. | |
| 5,949,061 A | 9/1999 | Guidash et al. | |
| 5,986,297 A | 11/1999 | Guidash et al. | |
| 6,064,431 A | 5/2000 | Ueno | |
| 6,069,377 A | 5/2000 | Prentice et al. | |
| 6,075,256 A | 6/2000 | Kaifu et al. | |
| 6,100,556 A | 8/2000 | Drowley et al. | |
| 6,107,655 A | 8/2000 | Guidash | |
| 6,127,697 A | 10/2000 | Guidash | |
| 6,160,281 A | 12/2000 | Guidash | |
| 6,177,293 B1 | 1/2001 | Netzer et al. | |
| 6,218,656 B1 | 4/2001 | Guidash | |
| 6,218,692 B1 | 4/2001 | Guidash | |
| 6,259,124 B1 | 7/2001 | Guidash | |
| 6,292,528 B1 | 9/2001 | Wieczorek et al. | |
| 6,295,336 B1 * | 9/2001 | Aach | A61B 6/542 378/108 |
| 6,297,070 B1 | 10/2001 | Lee et al. | |
| 6,307,195 B1 | 10/2001 | Guidash | |
| 6,320,617 B1 | 11/2001 | Gee et al. | |
| 6,323,476 B1 | 11/2001 | Guidash et al. | |
| 6,365,926 B1 | 4/2002 | Guidash | |
| 6,388,245 B1 | 5/2002 | Lee | |
| 6,429,718 B1 | 8/2002 | Lauter et al. | |
| 6,459,765 B1 * | 10/2002 | Ganin | A61B 6/00 378/108 |
| 6,466,265 B1 | 10/2002 | Lee et al. | |
| 6,466,266 B1 | 10/2002 | Guidash et al. | |
| 6,476,395 B2 | 11/2002 | Boerner et al. | |
| 6,486,504 B1 | 11/2002 | Guidash | |
| 6,501,064 B2 * | 12/2002 | Kole | H04N 5/3745 250/208.1 |
| 6,504,195 B2 | 1/2003 | Guidash | |
| 6,510,195 B1 | 1/2003 | Chappo et al. | |
| 6,552,323 B2 | 4/2003 | Guidash et al. | |
| 6,586,296 B1 | 7/2003 | Watt | |
| 6,587,146 B1 | 7/2003 | Guidash | |
| 6,597,025 B2 | 7/2003 | Lauter et al. | |
| 6,624,850 B1 | 9/2003 | Guidash | |
| 6,627,896 B1 * | 9/2003 | Hashimoto | H04N 5/32 250/370.01 |
| 6,633,334 B1 * | 10/2003 | Sakurai | H01L 27/14603 257/292 |
| 6,657,665 B1 | 12/2003 | Guidash | |
| 6,661,459 B1 * | 12/2003 | Koizumi | H01L 27/14609 257/233 |
| 6,671,347 B2 | 12/2003 | Tashiro et al. | |
| 6,707,066 B2 | 3/2004 | Morishita | |
| 6,710,804 B1 * | 3/2004 | Guidash | H04N 3/155 257/233 |
| 6,714,239 B2 | 3/2004 | Guidash | |
| 6,721,008 B2 | 4/2004 | Lee et al. | |
| 6,730,897 B2 | 5/2004 | Guidash | |
| 6,744,526 B2 | 6/2004 | McDermott et al. | |
| 6,763,129 B1 * | 7/2004 | Honda | G06K 9/40 382/132 |
| 6,800,836 B2 | 10/2004 | Hamamoto et al. | |
| 6,856,670 B2 | 2/2005 | Hoheisel | |
| 6,906,332 B2 | 6/2005 | Tashiro et al. | |
| 6,921,948 B2 | 7/2005 | Watt | |
| 7,015,479 B2 | 3/2006 | Haas et al. | |
| 7,053,354 B1 | 5/2006 | Luo et al. | |
| 7,075,061 B2 | 7/2006 | Spahn | |
| 7,102,117 B2 | 9/2006 | Hopper et al. | |
| 7,105,830 B2 | 9/2006 | Nagano et al. | |
| 7,113,096 B2 | 9/2006 | Spahn | |
| 7,129,979 B1 | 10/2006 | Lee | |
| 7,136,452 B2 * | 11/2006 | Spartiotis | A61B 6/14 250/370.09 |
| 7,151,287 B1 | 12/2006 | Scheffer et al. | |
| 7,180,073 B2 | 2/2007 | Tetsuo | |
| 7,180,075 B2 | 2/2007 | Brabec et al. | |
| 7,199,410 B2 | 4/2007 | Dierickx | |
| 7,202,481 B2 | 4/2007 | Spahn et al. | |
| 7,238,948 B2 | 7/2007 | Fritzler et al. | |
| 7,241,983 B2 | 7/2007 | Spahn | |
| 7,253,019 B2 | 8/2007 | Dierickx | |
| 7,266,177 B2 | 9/2007 | Spahn | |
| 7,271,391 B2 | 9/2007 | Kameshima | |
| 7,304,673 B2 | 12/2007 | Erhardt et al. | |
| 7,313,225 B2 * | 12/2007 | Mertelmeier | A61B 6/02 378/116 |
| 7,315,027 B2 | 1/2008 | Okada et al. | |
| 7,326,934 B2 | 2/2008 | Dorscheid et al. | |
| 7,326,935 B2 | 2/2008 | Klausmann et al. | |
| 7,327,823 B2 * | 2/2008 | Matsuura | A61B 6/032 378/8 |
| 7,336,763 B2 * | 2/2008 | Spartiotis | A61B 6/14 378/38 |
| 7,340,034 B2 * | 3/2008 | Hayashida | A61B 6/00 378/98 |
| 7,356,119 B2 * | 4/2008 | Anno | A61B 6/481 378/37 |
| 7,359,482 B2 | 4/2008 | Schmitt | |
| 7,365,016 B2 | 4/2008 | Ouellet et al. | |
| 7,408,195 B2 | 8/2008 | Meynants | |
| 7,408,238 B2 | 8/2008 | Shibayama | |
| 7,421,061 B2 * | 9/2008 | Boese | A61B 5/721 378/205 |
| 7,435,966 B2 | 10/2008 | Vogtmeier et al. | |
| 7,436,927 B2 | 10/2008 | Hempel | |
| 7,471,767 B2 * | 12/2008 | Spahn | G03B 42/02 378/101 |
| 7,480,082 B2 * | 1/2009 | Liang | G02B 3/005 250/208.1 |
| 7,489,760 B2 * | 2/2009 | Hemmendorff | A61B 6/502 378/37 |
| 7,498,650 B2 | 3/2009 | Lauxtermann | |
| 7,507,971 B2 | 3/2009 | Shibayama et al. | |
| 7,514,686 B2 | 4/2009 | Ogawa et al. | |
| 7,525,097 B2 | 4/2009 | Dorscheid et al. | |
| 7,550,728 B2 | 6/2009 | Spahn | |
| 7,566,169 B2 * | 7/2009 | Jakob | A61B 6/032 378/189 |
| 7,589,325 B2 | 9/2009 | Spahn | |
| 7,608,837 B2 | 10/2009 | Roizin et al. | |
| 7,622,719 B2 | 11/2009 | Spahn | |
| 7,627,086 B2 | 12/2009 | Vogtmeier | |
| 7,634,308 B2 * | 12/2009 | Ogawa | A61B 6/481 378/196 |
| 7,659,517 B2 | 2/2010 | Scheffer | |
| 7,663,115 B2 | 2/2010 | Korthout et al. | |
| 7,663,117 B2 | 2/2010 | Wittmann | |
| 7,675,097 B2 | 3/2010 | Adkisson et al. | |
| 7,705,317 B2 | 4/2010 | Miyaguchi | |
| 7,705,911 B2 * | 4/2010 | Kameshima | G01T 1/2018 323/267 |
| 7,718,945 B2 | 5/2010 | Sugiyama et al. | |
| 7,728,277 B2 | 6/2010 | Stevens et al. | |
| 7,728,303 B2 | 6/2010 | Mori et al. | |
| 7,742,559 B2 * | 6/2010 | Iordache | A61B 5/6843 378/195 |
| 7,755,689 B2 * | 7/2010 | Stevens | H04N 5/3575 250/208.1 |
| 7,776,638 B2 * | 8/2010 | Lavine | H01L 27/14632 257/E27.13 |

(56) References Cited

U.S. PATENT DOCUMENTS

| | | | |
|---|---|---|---|
| 7,783,000 B2 | 8/2010 | Kotooka | |
| 7,800,667 B2 | 9/2010 | Mizuno et al. | |
| 7,808,022 B1 | 10/2010 | Dierickx | |
| 7,838,994 B2 | 11/2010 | Shibayama et al. | |
| 7,858,915 B2 | 12/2010 | McCarten et al. | |
| 7,888,626 B2* | 2/2011 | Slinger | G01T 1/295 250/216 |
| 7,899,223 B2* | 3/2011 | Boese | A61B 5/0402 378/4 |
| 7,952,058 B2 | 5/2011 | Nomura et al. | |
| 8,018,067 B2 | 9/2011 | Steadman et al. | |
| 8,049,256 B2* | 11/2011 | Guidash | H01L 27/14634 257/292 |
| 8,067,743 B2 | 11/2011 | Ishii et al. | |
| 8,097,904 B2 | 1/2012 | Eminoglu et al. | |
| 8,193,501 B2* | 6/2012 | Rutten | H01L 27/14658 250/338.4 |
| 8,203,111 B2* | 6/2012 | Reshef | H01L 27/14609 250/208.1 |
| 8,207,485 B2* | 6/2012 | LePage | H01L 27/14603 250/208.1 |
| 8,253,214 B2* | 8/2012 | Guidash | H01L 27/14641 257/459 |
| 8,260,025 B2* | 9/2012 | Walimbe | A61B 6/5247 378/4 |
| 8,288,733 B2* | 10/2012 | Herrmann | G01T 1/2018 250/370.09 |
| 8,306,181 B2* | 11/2012 | Spartiotis | A61B 6/14 378/193 |
| 8,358,739 B2* | 1/2013 | Lu | H04N 5/32 378/8 |
| 8,368,027 B2* | 2/2013 | Ishii | G01T 1/2018 250/366 |
| 8,368,028 B2* | 2/2013 | Mori | A61B 6/06 250/370.09 |
| 8,396,188 B2* | 3/2013 | Liu | A61B 6/4233 378/62 |
| 8,483,358 B2* | 7/2013 | Allison | A61B 6/00 378/65 |
| 8,483,456 B2* | 7/2013 | Nagatsuka | A61B 5/08 382/128 |
| 8,513,612 B2* | 8/2013 | Levene | G01T 1/2985 250/370.08 |
| 8,542,794 B2* | 9/2013 | Miyamoto | A61B 6/00 250/354.1 |
| 8,546,859 B2* | 10/2013 | Maes | H01L 27/14609 257/292 |
| 8,633,572 B2* | 1/2014 | Vogtmeier | H01L 21/76898 257/621 |
| 8,693,632 B2* | 4/2014 | Allison | A61B 6/00 378/65 |
| 8,710,448 B2* | 4/2014 | Luhta | H01L 27/14618 250/370.09 |
| 8,729,652 B2* | 5/2014 | Heringa | G01T 1/2018 257/429 |
| 8,772,727 B2* | 7/2014 | Ruetten | G01T 1/24 250/336.1 |
| 8,779,366 B2* | 7/2014 | Wieczorek | G01T 1/2018 250/363.03 |
| 8,822,938 B2* | 9/2014 | Freund | H04N 5/32 250/208.1 |
| 8,859,975 B2* | 10/2014 | Tokura | G01T 1/2018 250/366 |
| 8,866,098 B2* | 10/2014 | Hayatsu | G01T 1/2018 250/370.09 |
| 9,000,388 B2* | 4/2015 | Tokura | G01T 1/2018 250/370.11 |
| 9,053,538 B2* | 6/2015 | Takahashi | G06T 5/002 378/87 |
| 9,082,182 B2* | 7/2015 | Sebok | G06T 7/0042 382/131 |
| 9,087,755 B2* | 7/2015 | Frach | H01L 27/1443 |
| 9,117,289 B2* | 8/2015 | Matsumoto | A61B 6/50 |
| 9,198,628 B2* | 12/2015 | Shimada | A61B 6/4291 |
| 9,201,150 B2* | 12/2015 | Ruetten | G01T 1/2018 |
| 9,320,485 B2* | 4/2016 | Brenner | A61B 6/037 |
| 2002/0131626 A1 | 9/2002 | Vogtmeier et al. | |
| 2004/0000630 A1 | 1/2004 | Spartiotis et al. | |
| 2004/0079865 A1 | 4/2004 | Hoshi | |
| 2005/0218353 A1 | 10/2005 | Liang | |
| 2006/0011853 A1 | 1/2006 | Spartiotis et al. | |
| 2006/0203114 A1 | 9/2006 | Xu | |
| 2006/0203959 A1 | 9/2006 | Spartiotis et al. | |
| 2007/0069144 A1 | 3/2007 | Kameshima | |
| 2007/0071171 A1 | 3/2007 | Hayashida et al. | |
| 2007/0176108 A1 | 8/2007 | Such et al. | |
| 2007/0236590 A1 | 10/2007 | Harris | |
| 2008/0042231 A1 | 2/2008 | Maes et al. | |
| 2008/0217546 A1 | 9/2008 | Steadman et al. | |
| 2009/0090846 A1 | 4/2009 | Stevens et al. | |
| 2009/0095912 A1 | 4/2009 | Slinger et al. | |
| 2009/0096046 A1 | 4/2009 | Heringa et al. | |
| 2009/0121146 A1 | 5/2009 | Luhta et al. | |
| 2009/0230289 A1 | 9/2009 | Lepage | |
| 2009/0321643 A1 | 12/2009 | Rutten et al. | |
| 2010/0034340 A1 | 2/2010 | Spartiotis et al. | |
| 2010/0074396 A1 | 3/2010 | Schmand et al. | |
| 2010/0127314 A1 | 5/2010 | Frach | |
| 2010/0140491 A1 | 6/2010 | Herrmann et al. | |
| 2010/0237228 A1 | 9/2010 | Reshef et al. | |
| 2010/0294940 A1 | 11/2010 | Wieczorek | |
| 2010/0329421 A1 | 12/2010 | Ruetten et al. | |
| 2011/0135057 A1 | 6/2011 | Mori et al. | |
| 2011/0168892 A1 | 7/2011 | Steadman et al. | |
| 2011/0240868 A1 | 10/2011 | Ruetten et al. | |
| 2012/0033868 A1 | 2/2012 | Ren et al. | |
| 2012/0037809 A1 | 2/2012 | Levene et al. | |
| 2012/0057678 A1 | 3/2012 | Lu et al. | |
| 2012/0097857 A1 | 4/2012 | Hayatsu et al. | |
| 2012/0189099 A1 | 7/2012 | Liu et al. | |
| 2014/0192960 A1* | 7/2014 | Sakaguchi | A61B 6/5235 378/98.2 |

FOREIGN PATENT DOCUMENTS

| | | |
|---|---|---|
| DE | 10024489 A1 | 11/2001 |
| DE | 10331522 A | 2/2005 |
| DE | 102005005903 A1 | 8/2006 |
| DE | 102005017944 A1 | 10/2006 |
| DE | 102005057538 A1 | 11/2006 |
| DE | 102005049228 A1 | 4/2007 |
| DE | 102006033716 A1 | 2/2008 |
| DE | 102008063309 A1 | 7/2010 |
| EP | 0530972 A2 | 3/1993 |
| EP | 0899946 A2 | 3/1999 |
| EP | 0948056 A2 | 10/1999 |
| EP | 1073265 A2 | 1/2001 |
| EP | 1119188 A2 | 7/2001 |
| EP | 1152471 A2 | 11/2001 |
| EP | 1237198 A1 | 9/2002 |
| EP | 1492168 A1 | 12/2004 |
| EP | 1530162 A2 | 5/2005 |
| EP | 1724828 A2 | 11/2006 |
| EP | 1870937 A1 | 12/2007 |
| EP | 1894246 A2 | 3/2008 |
| EP | 2002477 A2 | 12/2008 |
| EP | 2554119 A1 | 2/2013 |
| JP | 2001135268 A | 5/2001 |
| JP | 2002344809 A | 11/2002 |
| JP | 2004241298 A | 8/2004 |
| JP | 2007105480 A | 4/2007 |
| JP | 2009240656 A | 10/2009 |
| JP | 2010034520 A | 2/2010 |
| WO | 0158144 A1 | 8/2001 |
| WO | 2002061456 A2 | 8/2002 |
| WO | 2008045356 A2 | 4/2008 |
| WO | 2008073247 A1 | 6/2008 |
| WO | 2009072056 A2 | 6/2009 |
| WO | 2009138400 A1 | 11/2009 |
| WO | 2011129132 A1 | 10/2011 |

(56) References Cited

FOREIGN PATENT DOCUMENTS

| WO | 2011129133 A1 | 10/2011 |
| WO | 2011135486 A2 | 11/2011 |
| WO | 2013031667 A1 | 3/2013 |

OTHER PUBLICATIONS

PCT Search Report and Written Opinion issued in connection with corresponding Application No. US2015/043118 on Oct. 14, 2015.

* cited by examiner

MULTIPLE FRAME ACQUISITION FOR EXPOSURE CONTROL IN X-RAY MEDICAL IMAGERS

BACKGROUND

Medical imaging, for example mammography, may use low-energy X-rays as part of a diagnostic and a screening tool to examine patient tissue. Mammography, for example, is used for the detection of breast cancer, typically through detection of characteristic masses contained within the patient tissue. X-ray exposure time, during mammography, may be for several seconds.

Mammography requires that the patient tissue being examined be compressed using a dedicated compression unit (e.g., a parallel-plate compression unit) to even out the thickness of the patient tissue which may increase image quality by reducing a thickness of patient tissue that X-rays have to penetrate. However, compression of patient tissue can be painful for a patient and may result in the patient moving and, in turn, moving the patient tissue during imaging.

When the patient tissue moves during imaging, images acquired by mammography may be blurred and unusable for diagnosing the patient tissue. Since, determining if an image is blurred only occurs after the images are taken, and the images are examined by a technician, a patient may have to endure multiple exposures to X-rays until a clear image is obtained.

Therefore, it would be desirable to design a system and method that allows for determining if an image is blurred while the image is being taken.

BRIEF DESCRIPTION

According to some embodiments, a method to create a medical image is disclosed. The method comprises receiving a plurality of patient tissue images during an x-ray dose. Furthermore, during the x-ray dose, a determination is made if motion occurred in the plurality of patient tissue images. In a case that no motion is determined, a diagnostic image of the patient tissue comprising the plurality of patient tissue images is created. Other embodiments are associated with systems and/or computer-readable medium storing instructions to perform any of the methods described herein.

DRAWINGS

DETAILED DESCRIPTION

The present embodiments, as described herein, may relate to a multi-frame acquisition technique to address the above-mentioned problems. Instead of acquiring a single image after a long x-ray exposure window, the proposed system and method may relate to the acquisition of multiple (e.g., several tens) of images during an exposure window (e.g., a period of time when a patient is exposed to a single dose of X-rays). Patient motion may be detected in real time by tracking the images between successive frames and information associated with each image may be used to make intelligent decisions to control X-ray exposure.

Figure 1:
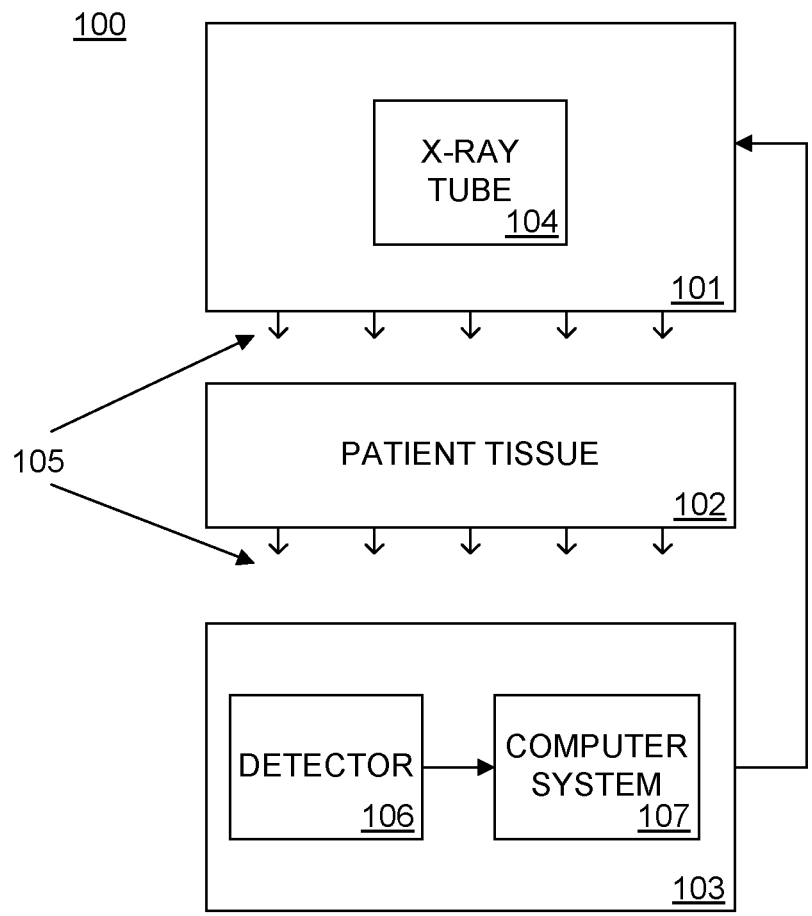
FIG. 1 is a block schematic diagram of a medical imaging system in accordance with some embodiments.
Figure 2:
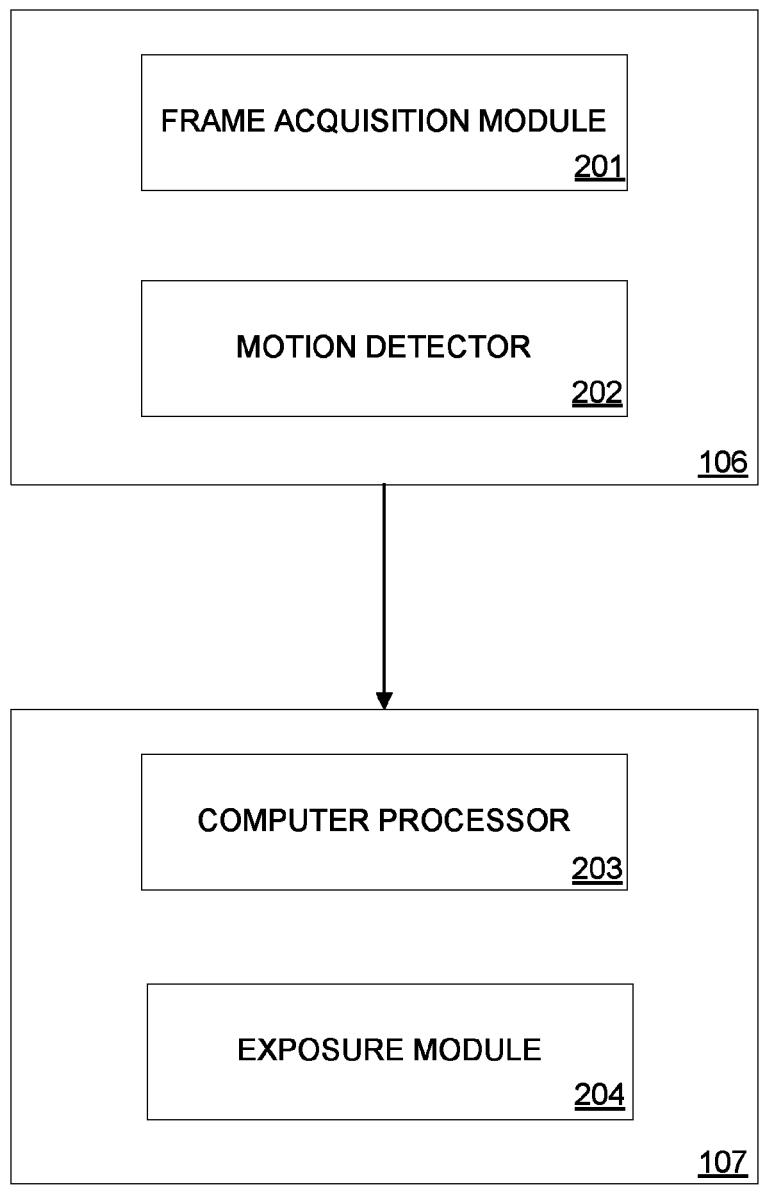
FIG. 2 illustrates components of medical imaging system in accordance with some embodiments.

Referring to FIG. 1 and FIG. 2 a medical imaging system 100 in accordance with some embodiments is shown. The medical imaging system 100 may comprise an X-ray generator 101 to transmit X-rays 105 through patient tissue 102. The X-rays 105 may be received at a receiver 103. The X-ray generator 101 may comprise an X-ray tube 104 to emit X-rays 105. The X-ray tube 104 may comprise a vacuum tube that produces X-rays 105. The patient tissue 102 may comprise an ensemble of similar cells from a same origin, such as, but not limited to, cells associated with breast tissue of a particular patient.

The receiver 103 may comprise a detector 106 and a computer system 107. As illustrated, the detector 106 and the computer system 107 may be internal to the receiver 103, however, in some embodiments, the computer system 107 may be external to the receiver 103. The detector 106 may comprise a semiconductor-based detector, such as a Complementary Metal Oxide Semiconductor ("CMOS") based detector. CMOS is a technology that may be used for X-ray medical imaging detectors because its ultra low electronic noise and fast frame read out capabilities may be used to implement high-performance X-ray detectors.

In some embodiments, the detector 106 may comprise a CMOS X-ray detector that includes an image sensor panel comprising a pixel array. On a top of the image sensor panel a scintillator (not shown) may be disposed. Each pixel in the pixel array may comprise a charge collecting device (e.g., a photodiode) and an electronic circuit to access a signal from the pixel. The pixel array may absorb most of the x-rays and transfer their energy into optical photons that may be efficiently detected by the image sensor underneath. This detection mechanism may be referred to as an "in-direct" mechanism because the X-rays are first converted to optical photons which are in turn detected by the image sensor.

The detector 106 may function as a "camera" that captures X-rays 105. For example, X-ray photons may be converted to electron-hole pairs in the semiconductor based detector and are collected to detect the X-rays 105. The computer system 107 may function as a controller to control the X-ray generator 101 based on input from the detector 106. For example, the detector 106 may determine, during a single dose of X-rays 105, if motion occurred during the capturing of a plurality of patient tissue images and the computer system 107, in response to an input indicating that motion was detected, may manage an X-ray exposure time used to obtain the plurality of patient tissue images as well as manage which of the plurality of patient tissue images to use to create a diagnostic image. For example, in a first case, the computer system 107 may discard images prior to a time when motion is determined by the detector 106 and increase a time of the X-ray dose when the motion is determined at a start of the X-ray dose. In a second case, the computer system 107 may stop the X-ray dose and generate an indication that the X-ray dose was stopped when the motion is determined by the detector 106 at a middle of the X-ray dose. In a third case, the computer system 107 may stop the X-ray dose and discard the images from at time when the motion was determined by the detector 106 when the motion is determined by the detector 106 at an end of the X-ray dose.

Referring to FIG. 2, in some embodiments, the detector 106 may comprise a frame acquisition module 201 and a motion detector 202. Furthermore, the computer system 107 may comprise a computer processor 203 and an exposure module 204 according to some embodiments. Instead of acquiring a single image after an X-ray exposure window, as in conventional systems, the frame acquisition module 201 may acquire multiple (e.g., several tens) of images during a single X-ray dose (e.g., exposure). The motion detector 202 may detect patient motion in real time by tracking an image between successive frames to determine if motion occurred. The information regarding motion may be used by the computer system 107 to make intelligent decision to control X-ray exposure by controlling the X-ray generator 101. In some embodiments, motion may be determined by subtracting a first of a plurality of patient tissue images from a second of the plurality of patient tissue images. In some embodiments, the first and second images of the plurality of patient tissue images may be sequential images. When subtracting images where no motion has occurred, the result of the subtraction may be zero (e.g., each pixel from a first image cancels out a pixel from a second image). However, if motion occurred in one of the images, a result of the subtraction may be a non-zero value (e.g., greater than zero or less than zero). In some embodiments, a degree of motion may be permissible to account for errors associated with imaging variances. In some embodiments, a threshold value may be used instead of zero to compensate for quantum noise associated with the X-ray process. In other embodiments, the comparison between images may be based on comparing a group of summed pixels from each image. Summing groups of pixels may suppress quantum noise associated with the X-ray process. In some embodiments, motion may be detected by analyzing a skin line to determine if the skin line has shifted.

As stated above, the computer system 107 may function as a controller to control the X-ray generator 101 based on input from the detector 106. When the detector 106 determines that motion occurred during the capturing of a plurality of patient tissue images, the computer processor 203 may determine, during the x-ray dose, when the motion occurred and the exposure module 204 may mange the X-ray generator 101 in response to the detection of motion. The computer processor 203 may discard images prior to a time when motion is determined by the detector 106 when the computer processor determines that the motion was at a start of the X-ray dose. In this case, the exposure module 204 may indicate to the X-ray generator 101 to increase a time of the X-ray dose to compensate for the earlier detected motion. The exposure module 204 may stop the X-ray dose being administered by the X-ray generator 101 and the computer processor 203 may generate an indication that the X-ray dose was stopped when the computer processor 203 determines that the motion determined by the detector 106 was during a middle portion of the X-ray dose. The exposure module 204 may stop the X-ray dose being administered by the X-ray generator 101 and the computer processor 203 may discard the images from a time when the motion was determined by the motion detector 202 when the computer processor 203 determines that the motion occurred at an end of the X-ray dose.

Figure 3:
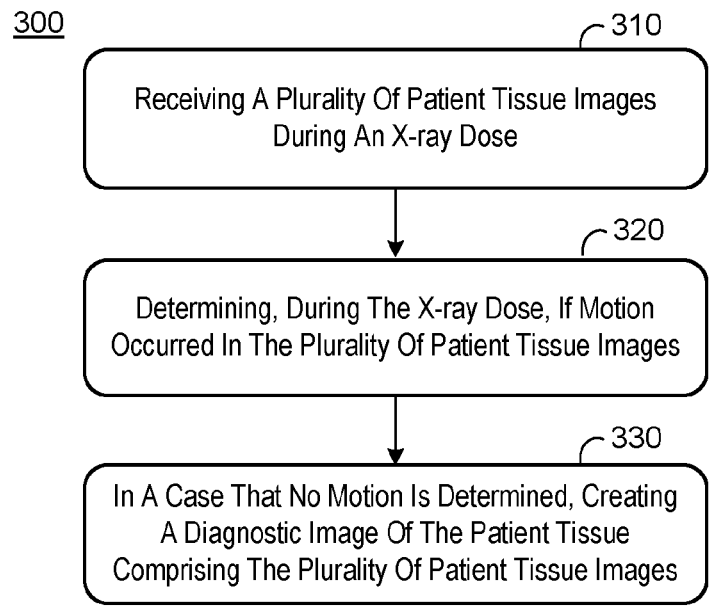
FIG. 3 illustrates a method associated with medical imaging in accordance with some embodiments.

FIG. 3 is a flow chart of a method 300 associated with creating a medical image in accordance with some embodiments. The flow charts described herein do not imply a fixed order to the steps, and embodiments described herein may be practiced in any order that is practicable. Note that any of the methods described herein may be performed by hardware, software, or any combination of these approaches. For example, a computer-readable storage medium (e.g., a non-transitory computer readable storage medium) may store thereon instructions that when executed by a machine result in performance according to any of the embodiments described herein.

At 310, a plurality of patient tissue images captured during an X-ray dose is received. The plurality of patient images may be received at a receiver, such as receiver 103 as described with respect to FIG. 1. The plurality of images may be captured by a detector 106, such as that described with respect to FIG. 2.

For illustrative purposes, and to aid in understanding features of the specification, three examples will now be introduced. These three examples are not intended to limit the scope of the claims. The first example relates to motion being detected in real time during a start of an X-ray dose. The second example relates to motion being detected in real time during a middle of the X-ray dose. The third example relates to motion being detected in real time during an end of the X-ray dose.

Figure 4:
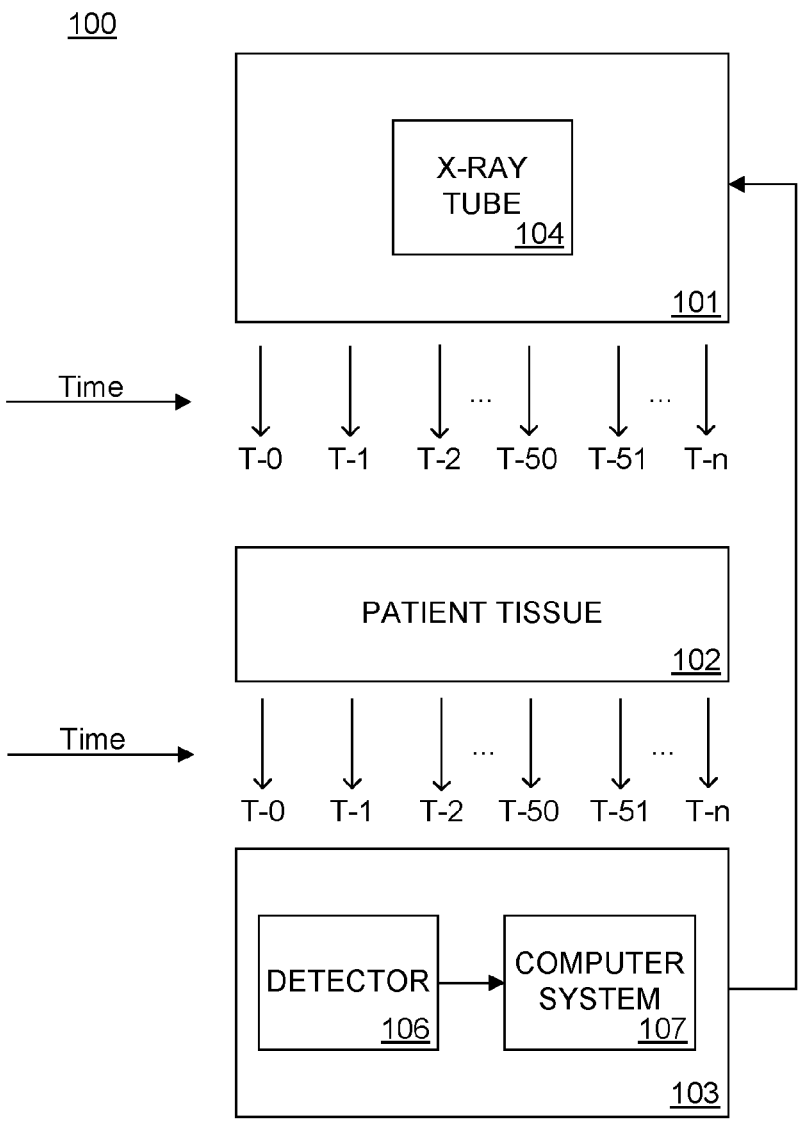
FIG. 4 is a block schematic diagram of a medical imaging system in accordance with some embodiments.

Now referring to FIG. 4, an embodiment of the medical imaging system 100 dispensing a single dose of X-rays 105 over time, as indicated by samples T-0 through T-n, is illustrated. Referring to the first example, a start of an X-ray dose maybe defined, for example, as a first 10% of the time allotted for the X-ray dose (e.g., a first 10% of the received samples). Thus, if the X-ray dose is to last for 2 seconds, the start of the X-ray dose may be defined as 0.2 seconds. The determination of a number of samples that may be captured during the start of the X-ray dose may be based on a sampling rate over a period of 0.2 seconds. The end of the X-ray dose may be defined as a last 10% of the time allotted for the X-ray dose (e.g., a last 10% of the received samples). Thus, if the X-ray dose is to last for 2 seconds, the end of the X-ray dose may be defined as the final 0.2 seconds of the X-ray dose. The determination of a number of samples during the end of the X-ray dose may be based on a sampling rate over a period of 0.2 seconds. The middle of the X-ray dose may be defined as greater than the first 10% of the time allotted for the X-ray dose and less than the last 10% of the time allotted for the X-ray dose. The parameters (e.g., percentages) for defining an end of the X-ray dose and the start of the X-ray dose may be user defined. In the present example, the start of the X-ray dose, as illustrated in FIG. 4, may be between time T-0 and T-2. The end of the X-ray dose, as illustrated in FIG. 4, may be between time T-50 and T-n. The middle of the X-ray dose, as illustrated in FIG. 4, may be between time T-2 and T-50.

Referring back to FIG. 3, at 320 a determination is made, during the X-ray dose, if motion occurred in the plurality of patient tissue images. The determination may be made in real time so that the dose of X-rays can be stopped should motion be detected. By stopping the dose of X-rays in a case when motion is detected, a patient may receive less X-rays than conventional methods. Determining if motion occurred between images may comprise subtracting a previous image from a present image, in real time, to determine if any motion has occurred between the images.

Continuing with the first example, the image at T-0 may be subtracted from the image at T-1. A determination will be made, in real time, if any motion can be detected. Likewise, determinations for the existence of motion will be made for samples associated with the second example and the third example.

At 330, in a case that no motion is determined, a diagnostic image of the patient tissue will be created, the diagnostic image comprising the plurality of patient tissue images. The diagnostic image may comprise a composite of the plurality of images.

However, in a case that motion is detected, a determination will be made as to if the motion occurred at a start of the X-ray dose, a middle portion of the X-ray dose, or at an end of the X-ray dose. In a case that motion is determined at the start of the X-ray dose, the images prior to a time when the motion was determined may be discarded and an amount of time to administer the X-ray dose may be increased. The amount of time to increase the X-ray dose may equal an amount of time when motion was detected at a start of the X-ray dose. For example, if motion was detected at 0.1 second into the X-ray dose, the total exposure time may be extended by 0.1 sec. In a case that motion is determined at the middle of the X-ray dose, the administration of the X-ray dose may be stopped and an indication that the X-ray dose was stopped may be generated and sent to an operator of the X-ray generator. The indication may notify the operator of the X-ray generator that the X-ray exposure may need to be restarted. In a case that motion is determined at the end of the X-ray dose, administration of the X-ray dose may be stopped and the images from at time when the motion was determined may be discarded. In this case, the diagnostic image of the patient tissue may comprise the plurality of patient tissue images taken prior to the time when the motion was determined and a patient may be exposed to less X-rays than conventional systems.

Figure 5:
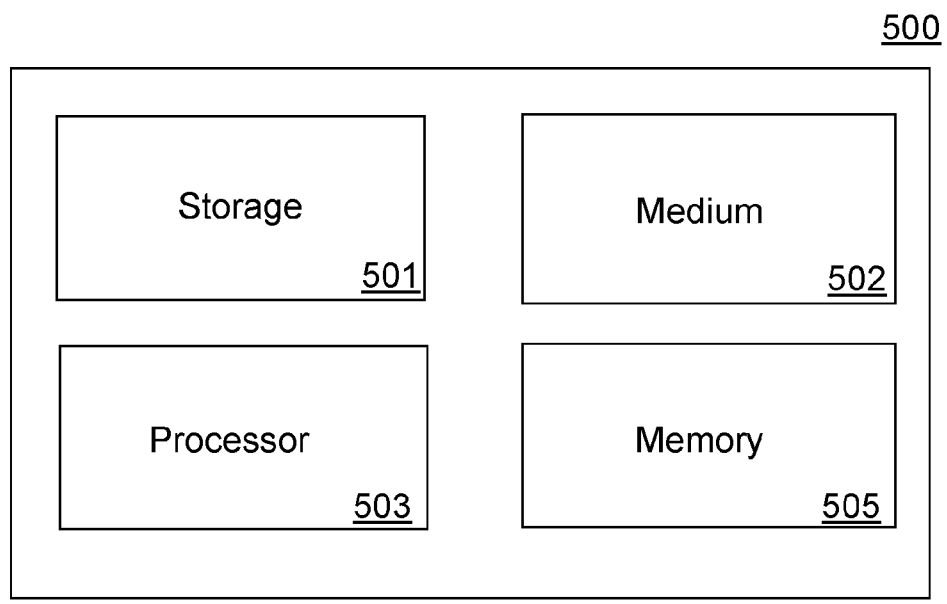
FIG. 5 illustrates components of a computing system in accordance with some embodiments.

Now referring to FIG. 5, an embodiment of a computer system 500 is illustrated. According to some embodiments, the computer system 500 may relate to an X-ray receiver system. The computer system 500 may comprise storage 501, a medium 502, a processor 503 and a main memory 505. According to some embodiments, the computer system 500 may further comprise a digital display port, such as a port adapted to be coupled to a digital computer monitor, television, portable display screen, or the like.

The storage 501 may store information (e.g., including information associated with X-ray exposures). The medium 502 may comprise any computer-readable medium that may store processor-executable instructions to be executed by the processor 503. For example, the medium 502 may comprise a non-transitory tangible medium such as, but is not limited to, a compact disk, a digital video disk, flash memory, optical storage, random access memory, read only memory, or magnetic media.

The processor-executable instructions may be stored in a compressed, uncompiled and/or encrypted format. The processor-executable instructions may furthermore include program elements, such as an operating system, a database management system, and/or device drivers used by the processor 503 to interface with peripheral devices.

The processor 503 may include or otherwise be associated with dedicated registers, stacks, queues, etc. that are used to execute program code and/or one or more of these elements may be shared there between. In some embodiments, the processor 503 may comprise an integrated circuit. In some embodiments, the processor 503 may comprise circuitry to perform a method such as, but not limited to, the method described with respect to FIG. 3.

The processor 503 communicates with the storage 501. The storage 501 may comprise any appropriate information storage device, including combinations of magnetic storage devices (e.g., a hard disk drive), optical storage devices, and/or semiconductor memory devices. The storage 501 may store a program for controlling the processor 503. The processor 503 performs instructions of the program, and thereby operates in accordance with any of the embodiments described herein. For example, the processor 503 may determine when motion occurred in a plurality of patient tissue images.

The main memory 505 may comprise any type of memory for storing data, such as, but not limited to, a Secure Digital (SD) card, a micro SD card, a Single Data Rate Random Access Memory (SDR-RAM), a Double Data Rate Random Access Memory (DDR-RAM), or a Programmable Read Only Memory (PROM). The main memory 505 may comprise a plurality of memory modules.

It is to be understood that not necessarily all such advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other advantages as may be taught or suggested herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method to create a medical image, the method comprising:
    receiving, by a computer system, a plurality of patient tissue images during an x-ray dose;
    determining, during the x-ray dose, if motion occurred in the plurality of patient tissue images;
    in a case that motion occurred, determining if the motion occurred at a start of the X-ray dose, a middle of the X-ray dose, or at an end of the X-ray dose; and
    in a case that motion occurred at the start of the X-ray dose, discarding the patient tissue images prior to a time when the motion occurred and increasing a time of the x-ray dose.

2. The method of claim 1, wherein determining if motion occurred comprises subtracting a first of the plurality of patient tissue images from a second of the plurality of patient tissue images.

3. The method of claim 1, further comprising:
    in a case that motion occurred at the middle of the X-ray dose:
    stopping the X-ray dose; and
    generating an indication that the X-ray dose was stopped.

4. The method of claim 1, further comprising:
    in a case that motion occurred at the end of the X-ray dose:
    stopping the X-ray dose; and
    discarding the patient tissue images from a time when the motion occurred.

5. A non-transitory, computer-readable medium storing instructions that, when executed by a computer processor, cause the computer processor to perform a method associated with creating a medical image, the method comprising:
    receiving, by a computer system, a plurality of patient tissue images during an x-ray dose;
    determining, during the x-ray dose, if motion occurred in the plurality of patient tissue images;
    in a case that motion occurred, determining if the motion occurred at a start of the X-ray dose, a middle of the X-ray dose, or at an end of the X-ray dose; and in a case that motion occurred at the start of the X-ray dose, discarding the patient tissue images prior to a time when the motion occurred and increasing a time of the x-ray dose.

6. The non-transitory, computer-readable medium of claim 5, wherein determining if motion occurred comprises subtracting a first of the plurality of patient tissue images from a second of the plurality of patient tissue images.

7. The non-transitory, computer-readable medium of claim 5, further comprising:
in a case that motion occurred at the middle of the X-ray dose:
stopping the X-ray dose; and
generating an indication that the X-ray dose was stopped.

8. The non-transitory, computer-readable medium of claim 5, further comprising:
in a case that motion occurred at the end of the X-ray dose:
stopping the X-ray dose; and
discarding the patient tissue images from a time when the motion occurred.

9. A medical imaging system, comprising:
an X-ray tube to generate a dose of X-rays;
a detector to capture a plurality of patient tissue images during the dose of X-rays; and
a computer system to:
(i) determine, during the dose of X-rays, if motion occurred during the capture of the plurality of patient tissue images;
(ii) manage the plurality of patient tissue images;
(iii) in a case that motion occurred during the capture of the plurality of patient tissue images, determine if the motion occurred at a start of dose of X-rays, a middle of the dose of X-rays, or at an end of the dose of X-rays; and
(iv) in a case that motion occurred at the start of the dose of X-rays, discarding discard the patient tissue images prior to a time when the motion occurred and increase a time of the dose of X-rays.

10. The medical imaging system of claim 9, wherein the computer system determines if motion occurred comprises subtracting a first of the plurality of patient tissue images from a second of the plurality of patient tissue images.

11. The medical imaging system of claim 9, wherein in a case that motion occurred at the middle of the X-ray dose, the computer system stops the X-ray dose and generates an indication that the X-ray dose was stopped.

12. The medical imaging system of claim 9, wherein in a case that motion occurred at the end of the X-ray dose, the computer system stops the X-ray dose, discards the patient tissue images from a time when the motion occurred.

13. The medical imaging system of claim 9, wherein the detector comprises CMOS-based detectors.

* * * * *